US 7,155,962 B2

(12) United States Patent
Knebel et al.

(10) Patent No.: US 7,155,962 B2
(45) Date of Patent: Jan. 2, 2007

(54) METHOD AND APPARATUS TO STUDY A SURFACTANT

(75) Inventors: Detlef Knebel, Berlin (DE); Matthias Amrein, Calgary (CA)

(73) Assignee: JPK Instruments AG, Berlin (DE)

( * ) Notice: Subject to any disclaimer, the term of this patent is extended or adjusted under 35 U.S.C. 154(b) by 0 days.

(21) Appl. No.: 10/477,832

(22) PCT Filed: May 17, 2002

(86) PCT No.: PCT/DE02/01828

§ 371 (c)(1),
(2), (4) Date: Mar. 30, 2004

(87) PCT Pub. No.: WO02/095367

PCT Pub. Date: Nov. 28, 2002

(65) Prior Publication Data

US 2004/0168506 A1    Sep. 2, 2004

(30) Foreign Application Priority Data

May 18, 2001  (DE) ................................ 101 25 754

(51) Int. Cl.
*G01N 13/02* (2006.01)

(52) U.S. Cl. .................. 73/64.52; 73/64.48; 73/64.51; 382/108

(58) Field of Classification Search ............... 73/64.48, 73/64.49, 64.52, 64.54; 95/149, 154; 382/100, 382/108
See application file for complete search history.

(56) References Cited

U.S. PATENT DOCUMENTS

| | | | | |
|---|---|---|---|---|
| 2,473,553 A | * | 6/1949 | Stokes ....................... | 73/64.52 |
| 3,483,737 A | * | 12/1969 | Schoettle et al. .......... | 73/64.52 |
| 3,525,255 A | * | 8/1970 | Orr, Jr. ...................... | 73/64.48 |
| 3,881,344 A | * | 5/1975 | Jobe .......................... | 73/64.51 |
| 3,913,385 A | * | 10/1975 | Jobe .......................... | 73/61.43 |
| 4,050,822 A | * | 9/1977 | Grat .......................... | 73/64.52 |
| 4,196,615 A | * | 4/1980 | Davis ........................ | 73/64.52 |
| 4,391,129 A | * | 7/1983 | Trinh et al. ................ | 73/64.48 |
| 4,523,456 A | * | 6/1985 | Baird et al. ................ | 73/64.48 |
| 4,569,226 A | * | 2/1986 | Matteson ................... | 73/64.52 |

(Continued)

FOREIGN PATENT DOCUMENTS

WO          WO 9216824 A     10/1992

(Continued)

OTHER PUBLICATIONS

Kwok et al., "Study on the surface tensions of polymer melts using axisymmetric drop shape analysis", Polymer Science and Engineering, May 1998, pp. 757-764.

(Continued)

*Primary Examiner*—Hezron Williams
*Assistant Examiner*—David A. Rogers
(74) *Attorney, Agent, or Firm*—Smith Patent Office

(57) ABSTRACT

The invention relates to a method of and an apparatus for studying properties, especially physical properties of a surfactant. A fluid is introduced in the form of a sample volume in another fluid which is immiscible with said fluid so that an interface is formed between the one fluid and the other fluid, at least in a partial area of a surface of the sample volume. The sample volume is configured so as to be axially symmetrical around a given defining axis, whereby the interface is formed axially symmetrically with respect to the given defining axis. The surfactant is spread across the interface to form a surface film in the area of the interface with the surfactant. Thereupon the surface film can by studied microscopically.

23 Claims, 6 Drawing Sheets

U.S. PATENT DOCUMENTS

| | | | | |
|---|---|---|---|---|
| 4,650,588 | A | * | 3/1987 | Diebold ............... 210/656 |
| 4,674,322 | A | * | 6/1987 | Stangeland ............. 73/32 A |
| 4,697,451 | A | * | 10/1987 | Matteson .............. 73/64.52 |
| 4,800,750 | A | * | 1/1989 | Enhorning ............. 73/64.48 |
| 4,874,426 | A | * | 10/1989 | Honda ................ 73/64.48 |
| 4,942,760 | A | * | 7/1990 | Almeida .............. 73/64.48 |
| 4,953,389 | A | | 9/1990 | Schurch |
| 5,218,841 | A | * | 6/1993 | Hool ................. 73/64.52 |
| 5,269,176 | A | * | 12/1993 | Hool ................. 73/64.52 |
| 5,394,740 | A | | 3/1995 | Schramm et al. |
| 5,479,816 | A | | 1/1996 | Richou et al. |
| 5,542,289 | A | * | 8/1996 | Hool et al. ........... 73/64.52 |
| 5,615,276 | A | | 3/1997 | Lin et al. |
| 6,832,506 | B1 | * | 12/2004 | Mason et al. .......... 73/64.53 |

FOREIGN PATENT DOCUMENTS

WO      WO 9423280 A1 * 10/1994

OTHER PUBLICATIONS

Enhorning, G., "Pulsating Bubble Technique for Evaluating Pulmonary Surfactant", J. Appl. Physiol. 1977, pp. 198-203, vol. 43, No. 2.

Lösche, M. et al., "Fluorescence Microscope to Observe Dynamical Processes in Monomolecular Layers at The Air/Water Interface", Rev. Sci. Instrum., Dec. 1984, pp. 1968-1972, vol. 55, No. 12.

Malcolm, B., "The Flow and Deformation of Synthetic Polypeptide Monolayers during Compression", Journal of Colloid and Interface Science, Apr. 1985, pp. 520-529, vol. 104, No. 2, Academic Press, Inc.

Schurch, S. et al., "A Captive Bubble Method Reproduces The In Situ Behavior of Lung Surfactant Monolayers", J. Appl. Physiol., 1989, pp. 2389-2396, vol. 67, No. 6, The American Physiological Society.

Ulman, A., "An Introduction to Ultrathin Organic Films From Langmuir-Blodgett to Self-Assembly", 1991, pp. 102-107, Academic Press.

Colton, R. et al., "Scanning Probe Microscopy", Current Opinion in Chemical Biology, 1997, pp. 370-377, vol. 1, Current Biology Ltd.

Putz, G. et al., "A Spreading Technique for Forming Film in a Captive Bubble", Biological Journal, Nov. 1998, pp. 2229-2239, vol. 75, Biological Society.

* cited by examiner

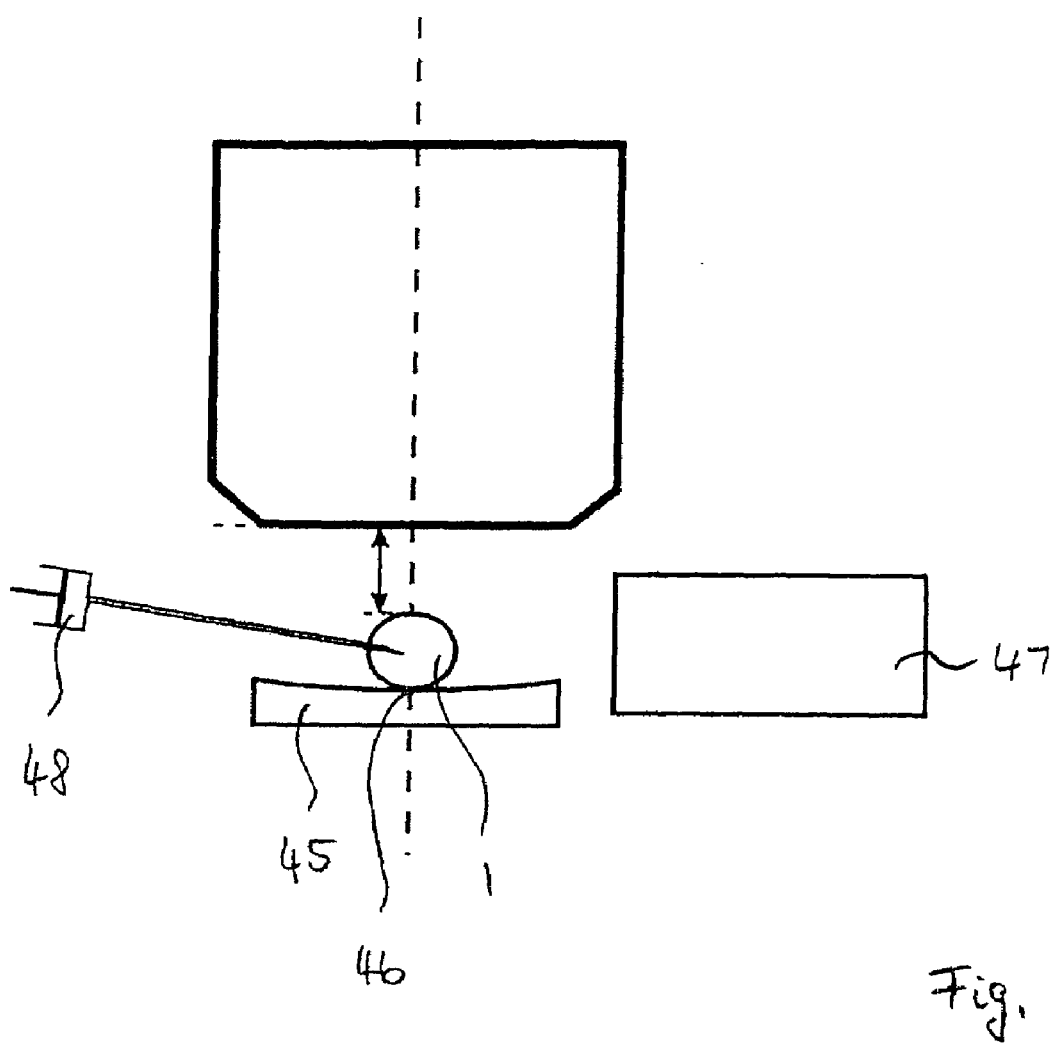

METHOD AND APPARATUS TO STUDY A SURFACTANT

The invention relates to a method of and an apparatus for studying a surface active agent (surfactant).

Surfactants form a molecular film at interfaces between two immiscible fluids. They allow targeted formation of molecularly defined layers; and they have gained considerable importance in non-linear optics, for instance. Surface active biological macromolecules (lung surfactants), for example, are a functional component of the human lung, and in life sciences they serve as a model of a plasma membrane. The film pressure Π of the surfactant counteracts the surface tension of the interface. For example, the relationship indicated below is valid for the interface between water and air:

$$\gamma = \gamma_0 - \Pi \quad (1)$$

wherein $\gamma_0$ is the surface tension of pure water (~72 mN/m at 25° C.) and $\gamma$ is the resulting surface tension of an interface with a film on top. A property in this context is the increasing film pressure as the mean area per molecule decreases, the surface tension going down correspondingly. This relationship develops in a characteristic way depending on the surfactant, and it is recorded at constant temperature in a so-called pressure: area isotherm which can be measured, for instance, by means of a captive bubble surfactometer.

A captive bubble surfactometer is suitable for determining the surface tension of an interface by a mathematical operation based on the bubble geometry of a gas bubble in a liquid. One method of determining the surface tension is the so-called drop shape analysis ADSA—Axisymmetric Drop Shape Analysis, as described e.g. by Kwok et al. in the journal "Polymer Engineering and Science" (1998) 38:757. For its buoyancy in liquid, the gas bubble is driven to a slightly domed agar roof and thus fixed. The volume can be changed by varying the chamber pressure, thereby also changing the shape of the gas bubble. This may be drawn upon to derive the corresponding surface tension. For further details of the captive bubble surfactometer, we refer to the publication by Schurch et al. "A captive bubble method reproduces the in situ behavior of lung surfactant monolayers" in J. Appl. Physiol. (1989) 67: 2389–96.

Another method of measuring pressure:area isotherms is employed in a pulsating bubble surfactometer, as described, for instance, by Enhorning in an article entitled "A pulsating bubble technique for evaluating pulmonary surfactant", J. Appl. Physiol. (1977) 43: 198–203. In one embodiment a capillary tube filled with gas is immersed in a liquid which is contained in a closed vessel. Subsequently the liquid volume in the vessel is diminished by a predetermined quantity. That causes a gas bubble of corresponding volume to exit from the capillary tube into the liquid. The interface tension at the interface between the gas and the liquid can be calculated by a mathematical operation.

The basis for calculating the surface tension is the Laplace formula according to which $\Delta p$ describes the pressure differential between the two fluids, $\gamma$ is the surface tension and $c_1$ and $c_2$ are the main radii of curvature of the surface $$\Delta p = \gamma(c_1 + c_2) \quad (2)$$

In both methods described above, the gas may be replaced by a less dense liquid which is immiscible with the liquid in which otherwise the gas bubble is introduced.

The pressure area isotherms, as determined by the methods described above provide information regarding thermodynamic phenomena, such as phase conversions of the first or higher orders, miscibility in case of multicomponent systems, etc. in connection with the surface film which comprises the surfactant. The molecular architecture of the surface film during this compression is highly interesting since it permits conclusions to be drawn as to the basic molecular principles of the characteristic behavior of a substance. It was found that a surface film in the area of the interface between two fluids may contain phase interfaces between molecules in different physical states; with mixed films, a characteristic distribution of the molecules may occur within the surface film, etc. The lung surfactant, for example, forms a complex three-dimensional molecular architecture which is directly related to the function thereof and of which only bits are understood so far.

There is a method of studying the structure of surfactants in surface films which provides for fluorescent marking of certain components and subsequent observation through a fluorescent light microscope, cf. Lösche et al. "Fluorescence microscope to observe dynamical processes in monomolecular layers at the air/water interface", (1984) 55: 1968–1972). In order to be able to associate a structure with a particular state of the film, this kind of study at the gas/liquid interface is carried out with a so-called film balance (weighing device). This means that a substance is spread at the gas/liquid interface of a trough filled with a liquid (typically with an extension of the interface of some square centimeters) and is then compressed by means of a movable barrier (cf. e.g. Ulman, A., "An introduction to ultrathin organic films", Academic Press, Boston, 1991, page 442). For epifluorescent light microscopy, an objective lens is placed on the film balance at a central position above the surface film.

It is a disadvantage of this method that the surface film on the film balance is subjected to flows which may be very strong, especially at low film pressures, but which may occur spontaneously at high film pressures, too. Hereby the microscopic investigation of the surface film is impaired quite considerably. Moreover, the system is extremely sensitive to disturbances originating from the environment, such as circulating air in the laboratory or vibrations of the building because it has a large interface exposed to the surroundings and because the liquid in the trough tends to oscillate. This makes it impossible to observe the behavior of individual structures over time; at least, however, it requires expensive shielding of the equipment from the surroundings.

Variations of the interface dimension lead to further flows and tensions in the surface film, as described, for instance, by Malcom, "The Flow and Deformation of Synthetic Polypeptide Monolayers during Compression", J. Colloid Interface Sci. (1985) 104:520. Furthermore, the surface film is shifted with respect to the objective of the light microscope upon compression or expansion so that the structures of interest disappear from the field of view under investigation.

At high film pressures, often so-called creeping occurs on a film balance: instead of further compaction of the molecules, they move away from the water/air interface. The molecules are pushed under the movable barrier, for instance.

It is, therefore, an object of the invention to indicate an improved method and an improved apparatus with which surface films including a surfactant are available in such form at an interface between two fluids for microscopic study that the study can be carried out with greater precision and less susceptibility to errors.

As an essential concept, the invention comprises the idea of introducing one fluid in the form of a sample volume in another fluid which is immiscible with the one fluid so that an interface forms between the one fluid and the other fluid at least in a partial area of a surface of the sample volume, the sample volume becoming configured axially symmetrically around a given defining axis so that the interface will be axially symmetrical with respect to the given defining axis. The surfactant is spread across the interface to form a surface film in the area of the interface.

The microscopic study of the surface film containing the surfactant enjoys several advantages over the prior art. The interface between the two fluids is characterized by great mechanical and temporal stability. The sample volume of the one fluid is well shielded by the other fluid from acoustic disturbances and thermal variations in the environment. For instance, when the pressure in the measurement chamber differs from ambient pressure almost complete acoustic decoupling from the surroundings is achieved. When a very small sample volume is selected the tendency of the interface to oscillate is reduced dramatically in comparison with measuring by means of the film balance. Thus the complicated and expensive shielding of the equipment from the environment may be dispensed with. High resolution microscopies may be applied, such as raster scan microscopy (cf. Colton et al., "Scanning probe microscopy", Curr. Opin. Chem. Biol. (1997) 1:370–377).

Suitable arrangement will cause the surface film to contract and expand, respectively, symmetrically with respect to the given defining axis when the area is changed.

The above mentioned creeping of the surface film at high film pressure is completely avoided when the captive bubble surfactometer is used.

The stabilization achieved of the surface film permits an investigation of dynamic structural changes of the surfactant in the surface film at the interface between the two fluids. Moreover, microscopy by high resolution methods is applicable, as compared to the known study which uses the film balance. Furthermore, an active interface film so far can be subjected to light microscopic study on a gas/liquid boundary layer only.

An axially symmetric sample volume with the resulting axially symmetric interface can be obtained, for instance, by introducing the one fluid of lower density into the other fluid of higher density and limiting the buoyancy of the sample volume by means of an element whose properties approach those of the other fluid so that the interface between the two fluids is not influenced substantially in the area of the surface of the sample volume. Giving said element the configuration of a dome-shaped roof can cause self-centering of the sample volume in a horizontal plane. Other means for centering may be provided as well, for example, some mechanical adjustment in the horizontal plane. The introduction of the one fluid may be accomplished, for example, through a valve and/or a syringe. Of course, other ways of introduction are conceivable as well.

Alternatively, the one fluid may enter the other fluid from a capillary means. With this embodiment, the interface or boundary layer is not closed in an area where the sample volume and the capillary means contact each other. With both embodiments described, the surface tension can be measured by analyzing the shape of the interface.

The possibility of purposively varying the interface can be materialized with the embodiment providing for the sample volume of the one fluid to be introduced in the other fluid without a capillary means in that the pressure is varied, as is known in the context of the captive bubble surfactometer.

When introducing the sample volume by a capillary means, the variation of the interface can be achieved by applying the principle underlying the pulsating bubble surfactometer described above. In this case the volume of the other fluid is varied, whereby a volume of the one fluid corresponding to the variation either enters or exits the capillary means.

A lateral image of the sample volume may be taken with the aid of an optical observation means from a direction at right angles to the axial axis of symmetry of the sample volume in order to measure the surface tension between the two fluids which are influenced by the surface film on the sample volumes. Various mathematical operations may be applied to calculate the surface tension either precisely or at close approximation.

Alternatively, acoustic excitation of the sample volume may be selected for measuring the surface tension. As the resonant frequencies due to capillary forces depend on the surface tension they can be determined from a frequency spectrum. With one embodiment, the spectrum may be detected optically by observing standing waves at certain frequencies. Sufficient excitation energy must be applied for the amplitudes to become big enough for optical detection. Amplitudes in the nm range can be detected when using a raster scan microscope. Selectively, the spectrum also might be detected by absorption measurement because a particularly great amount of energy for the starting of oscillations is absorbed in resonance and scattered isotropically, at least in part. A recording could be made by means of a microphone, for instance.

In case the interface between the two fluids is to be varied, according to an embodiment of the invention, such as to permit the study of area-induced changes in the surface film, the one fluid which is the one forming the sample volume, preferably is a gas. Both fluids are disposed in a pressure-tight chamber. The pressure is varied to vary the volume and thus the surface of the sample volume which consists of gas. If the sample is to be observed through a light microscope an objective lens must be approached to the sample volume. For optimum observation, the objective lens may be optically adapted to the other fluid, i.e. it may be suitable to be immersed in water if the other fluid is water into which it is immersed. It is likewise possible to watch the sample volume in the airtight chamber through a transparent plate. The objective lens of a light microscope may be replaced by the probe of a raster scan microscope or the observation means of another microscopic technique.

A convenient further development of the invention may provide for the object plane of the microscope used for studying the surface film to be always located at the lowest point, also referred to as apex, of the surface of the sample volume. To this end, it is possible to shift the sample volume in the direction of the optical beam path. Also, displacement at right angles to the optical axis may be provided in order to move the apex onto the optical axis.

Further advantages and convenient further developments of the invention will become apparent from the description below of embodiments made with reference to a drawing, in which:

FIG. 6 is a diagrammatic illustration to explain another method of studying a surfactant in a surface film.

Figure 1:
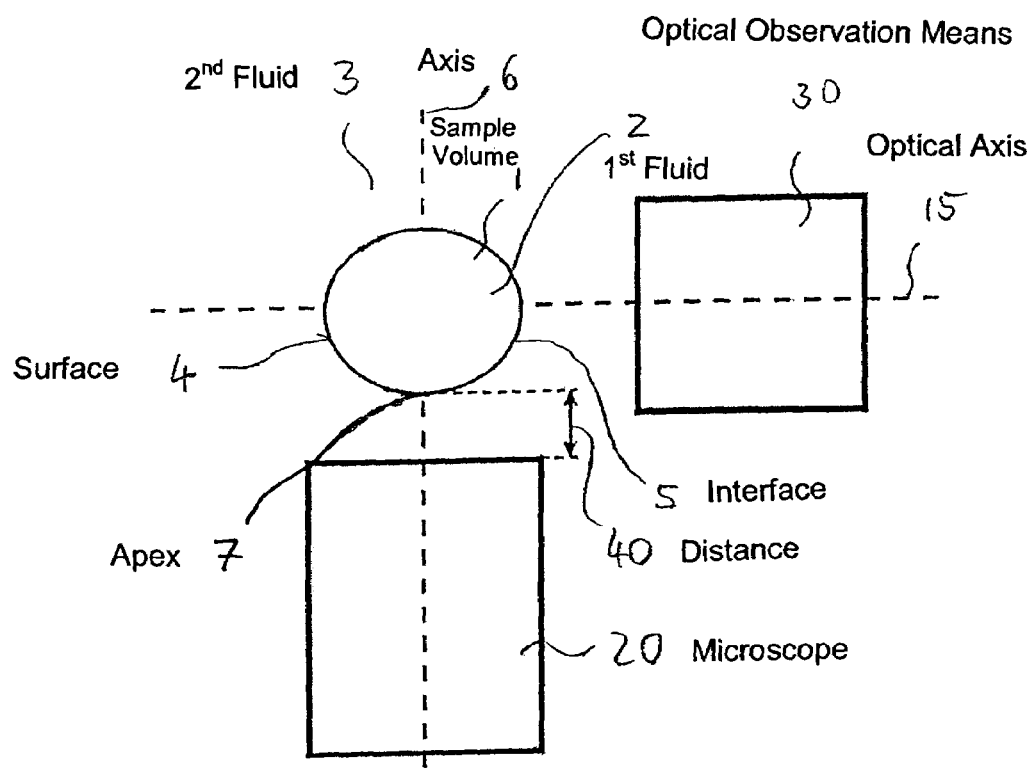
FIG. 1 is a diagrammatic illustration to explain a method of studying a surfactant in a surface film.

FIG. 1 gives a digrammatic illustration to explain a method of studying a surfactant in a surface film. A sample volume 1 of one fluid 2 is surrounded by another fluid 3. An interface 5 is formed between the two fluids 2, 3 on a surface 4 of the sample volume 1. One or more surfactants whose physical properties are to be studied are applied in the region of the interface 5. The surfactants applied form a surface film on the sample volume 1 in the region of the interface. The sample volume 1 and, as a consequence thereof, the interface are configured axially symmetrically with respect to an axis 6. Due to the axial symmetry, flowing of the surface film is impossible provided the molecules of the surface film formed of the surfactant are not soluble in either of the two fluids 2, 3 and the two fluids are not miscible.

A microscope 20 of which the optical axis conveniently coincides with the axis 6 is provided for microscopic observation of the surface film. Thus an apex 7, i.e. the lowest point of the sample volume 1 or interface 5 can be positioned opposite the microscope 20. A distance 40 between the microscope 20 and the apex 7 is kept conveniently constant during the measurement.

An optical observation means 30 of which the optical axis, marked 15, extends at right angles to the axis 6 allows the surface tension of the surface film to be determined based on the shape of the interface 5. The axis 15 need not pass through the center of the sample volume 1. It merely needs to be assured that the entire outline or a part of the outline sufficient to determine the surface tension of the sample volume can be seen. The three-dimensional shape can be determined on the basis of the outline in view of the axial symmetry of the sample volume 1 with respect to the axis 6.

Figure 2:
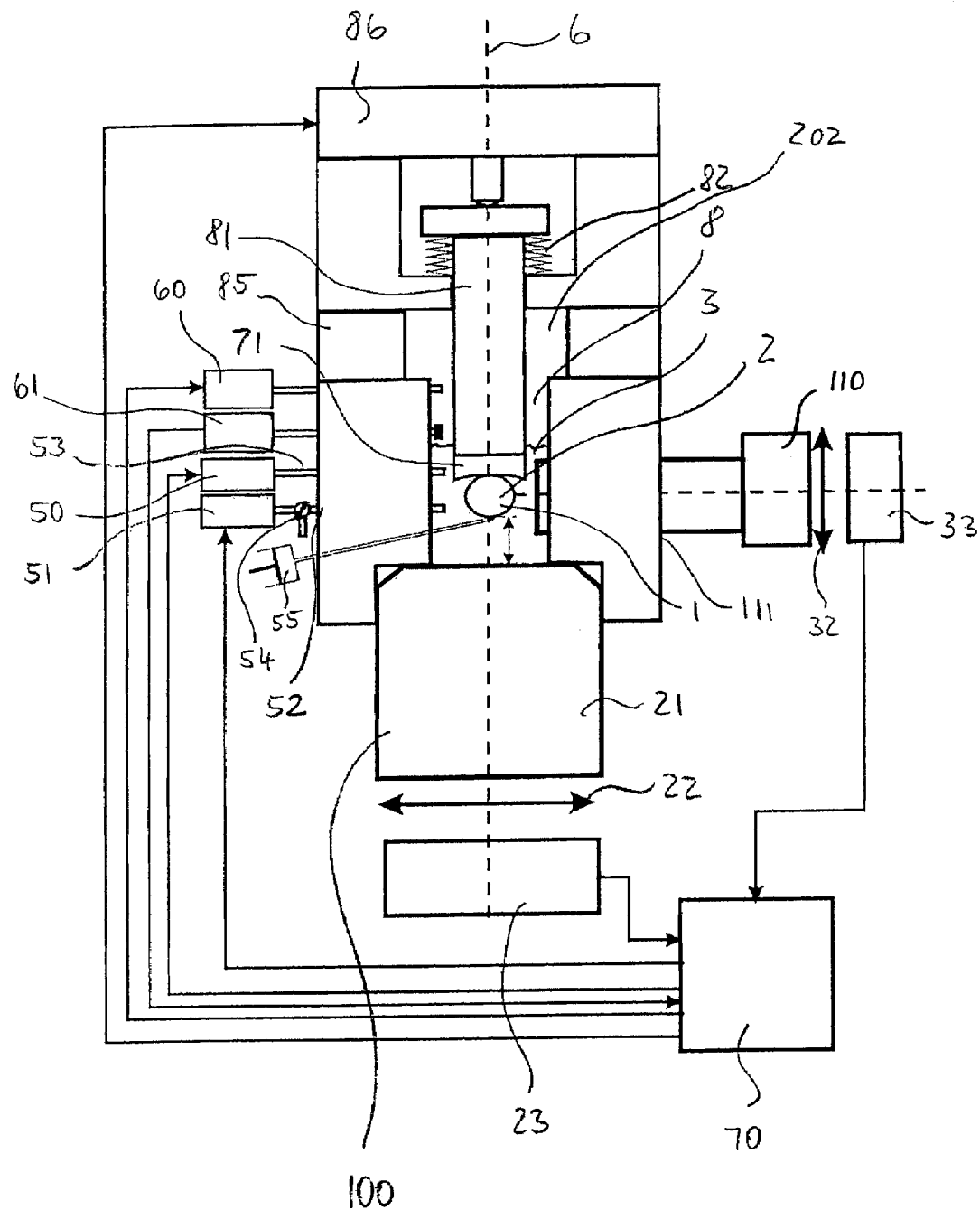
FIG. 2 is a diagrammatic illustration of a captive bubble surfactometer for utilizing the method of studying a surfactant.

FIG. 2 is a diagrammatic presentation of a captive bubble surfactometer for utilizing the method to study the surfactant. Fluid 3 in this case, for example, is water which is filled in an airtight chamber 8. Fluid 2 is a gas. Buoyancy causes the sample volume 1 to be pressed against a hydrophilic dome-shaped roof 71 which may be agar gel, for example, and the interface 5 is formed which is axially symmetrical with respect to the axis 6. In the embodiment, the sample volume 1 has a diameter of from about 100 μm to 300 μm. In principle, however, also smaller and greater dimensions are conceivable. The agar gel 4 and its configuration retain the sample volume 1 in the chamber 8.

The fluid 3 may be supplied and exchanged, if desired, through dispenser pumps 50, 51. Feeding from the dispenser pumps 50, 51 into the chamber 8 takes place through pressure and vacuum tight passages 52, 53 from the high pressure liquid chromatography (HPLC). In addition, fluid 2 for making up the sample volume 1 may be fed through a valve 54. Furthermore, it is possible to introduce the surfactant through the same valve 54 for spreading on the interface 5. Alternatively, the surfactant may be injected through a syringe 55 against the interface 5 (cf. Putz et al., "A spreading technique for forming a film in a captive bubble in a surfactometer", Biophysical Journal (1998) 75:2229–39. After the spreading, the syringe 55 must be removed to allow unimpeded expansion and observation of the sample volume 1.

The sample volume 1 may be displaced in the directions of the X- and Y-axes by means of a mechanical stage 85 capable of slide motion, either by hand or by a motor, and in the direction of Z-axis by a motor driven micrometer screw 86 or by any other adjustment means. Mechanical contact with the motor driven micrometer screw 86 is obtained through a plunger 81, as may be taken from FIG. 2. A spring 82 establishes mechanical contact with the motor driven micrometer screw 86. In the case of an alternative embodiment, shifting in the direction of the Z-axis may be accomplished by means of a piezo element. In that event the spring 82 serves biasing purposes.

With the embodiment shown in FIG. 2, the sample volume 1 is investigated microscopically through a light microscope 100. The light microscope 100 may be an epifluorescent light microscope, for example, which is operated selectively, either confocally or conventionally. It means that an objective 21 is immersed in the fluid 3. The microscopic image which, for instance, may be a fluorescence distribution, is imaged by a lens 22 on a CCD chip 23, digitized, and subjected to evaluation by a evaluation means 70 which may be a personal computer, for example.

Examination of the sample volume 1 from the side likewise is provided to determine the surface tension of the surface film on the sample volume 1. This is accomplished by means of a borescope 110. A passage 111 is devised as an HPLC passage. To determine the surface tension, the borescope 110 detects the outline of the sample volume 1. A lens 32 focusses the image on a CCD chip 33 for subsequent digitizing. The digitized image is evaluated by the evaluation means 70. The surface tension between the two fluids which are influenced by the surface film at the sample volume 1 can be determined by application of the ADSA algorithm. The evaluation means 70 assigns each microscopic image its respective surface tension and stores the same.

A software driven disperser pump 60 permits varying the dimension of the sample volume 1 and, thereby, that of the interface 5. The pressure in the chamber 8 is controlled by a pressure gauge 61 which likewise may be read by adequate software. Passages 200, 201 of the disperser pump 60 and pressure gauge 61 are designed as HPLC passages. The disperser pump 60 varies a gas pressure inside a space 202 above the fluid 3 in the chamber 8. Hereby, the volume of the sample volume is changed. Usually the disperser pump 60 is used to generate negative pressure, however, it may also be employed to apply positive pressure.

The motor driven micrometer screw 86 may be actuated to shift the sample volume 1 in the direction of the Z-axis so as to keep the distance 40 constant between the apex 7 of the sample volume 1 and the objective 21, even though the volume of the sample volume 1 changes.

All the functions described in the arrangement illustrated in FIG. 2 are served by the evaluation means 70 through a uniform user interface. In particular, the microscopic images taken by the light microscope 100 and the borescope 110 are integrated as functions of the uniform user interface. If a defined amount of substance is spread at the interface 5, the surface tension of the surface film can be calculated as a function of the mean area per molecule. That permits conclusions to be drawn, for instance, regarding structure-function relations of the spread surfactant.

Figure 3A:
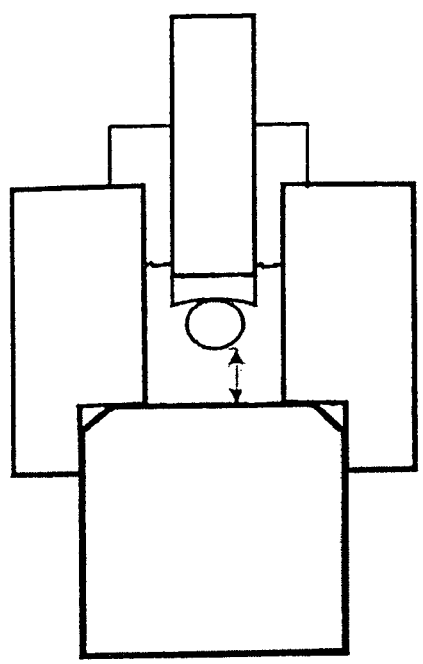
FIG. 3 is a diagrammatic illustration to explain a volume variation and refocussing in combination with the captive bubble surfactometer shown in FIG. 2.
Figure 3B:
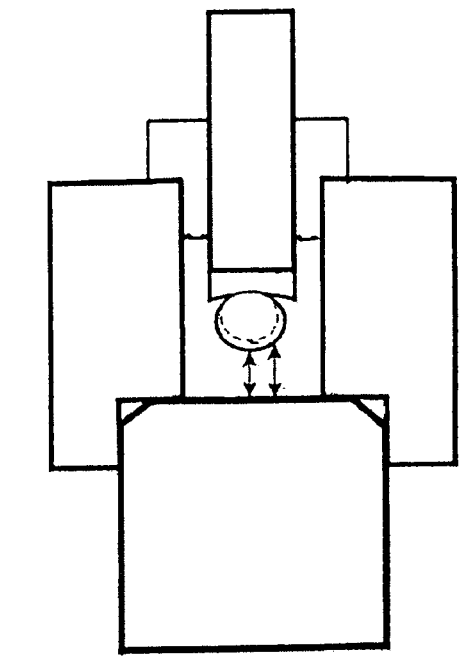
Figure 3C:
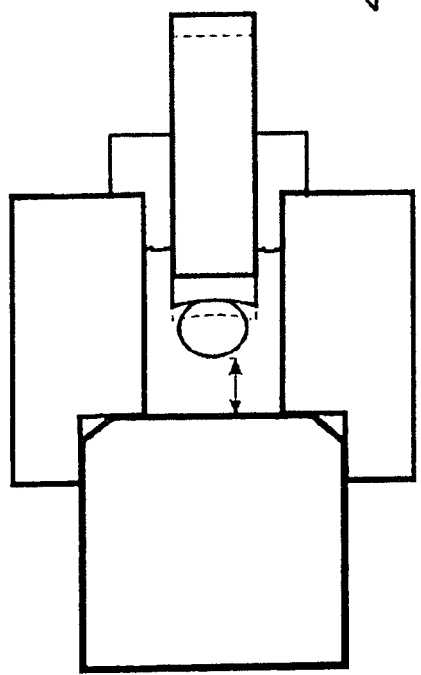

FIGS. 3A to 3C are diagrammatic presentations intended to explain a variation in volume and readjustment in connection with the captive bubble surfactometer shown in FIG. 2. FIG. 3A illustrates the starting situation with the arrangement according to FIG. 2. To obtain this starting situation, for example, the chamber 8 is filled with about 100 μl of a buffer. Moreover, the sample volume 1 is injected at a diameter of about 100 μm, for example. The diameter in this context refers to the largest extension of the sample volume 1 in the direction of the X-axis, i.e. perpendicular to the optical axis 6. Subsequently, the diameter is increased to about 300 μm in the selected example by applying negative pressure. Observation through the light microscope 100 and the borescope 110 begins, and the sample volume 1 is moved onto the optical axis. Then the apex 7 of the sample volume 1 is moved into the focal plane of the light microscope 100. Now the surfactant is injected. The adsorption of the surfactant is measured structurally by the light microscope 100 and functionally by the borescope 110 (reduction of surface tension).

The size of the sample volume 1 is varied, as indicated in FIG. 3B. In the example shown, the volume of the sample volume 1 is increased, whereby the distance 40 of the apex 7 from the objective 21 becomes smaller. The original shape of the sample volume 1 is illustrated in discontinuous lines in FIG. 3B. The original distance 40 must be reestablished to obtain a sharply focused optical image by means of the light microscope 100. This is achieved by means of the plunger 81, as illustrated in FIG. 3C. In FIG. 3C the original position of the plunger 81 is indicated in discontinuous lines.

Figure 4:
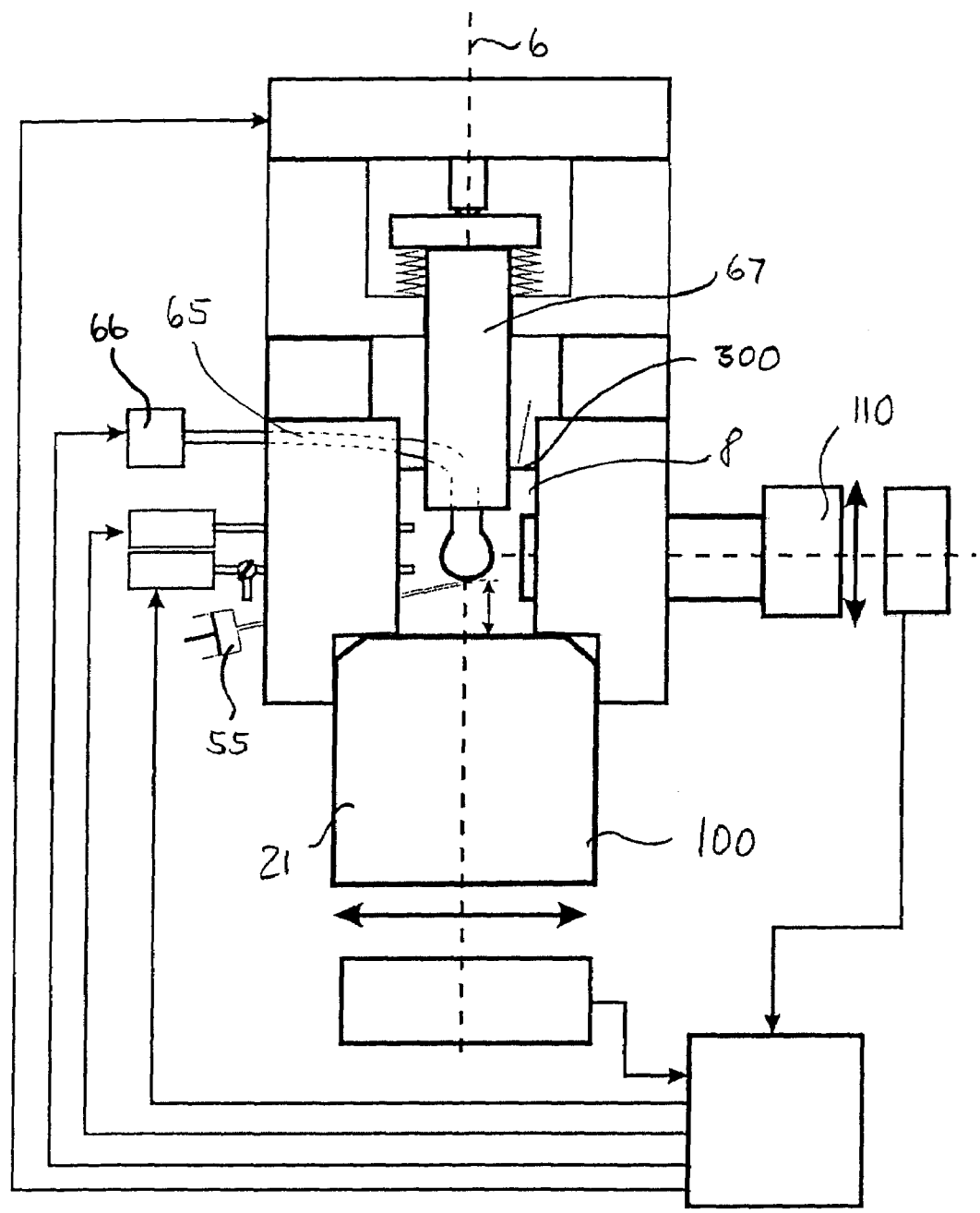
FIG. 4 is a diagrammatic illustration of a pulsating bubble surfactometer for utilizing the method of studying a surfactant.

FIG. 4 is a diagrammatic presentation of a pulsating bubble surfactometer for utilizing the method of studying the surfactant. Other than with the arrangement shown in FIG. 2, the chamber 8 is covered by a roof 300 and completely filled with fluid 3 which, in this case, is a liquid. Fluid 2 may be a gas or a liquid which is immiscible with fluid 3. In the embodiment according to FIG. 4, the fluid 2 does not form a closed interface 5. Instead it exits from a hose 65 adapted to be positioned, for instance, by a plunger 67. The hose 65 communicates with a chamber volume 66 which may be embodied, for example, by a syringe filled with a gas and including a locking ring.

Variation of the sample volume 1 is obtainable, for instance, by movement of the plunger 67. Another possibility would be by feeding gas through the syringe 55.

Creeping which, in principle, is possible with the embodiment as illustrated in FIG. 4, in other words emigration of the molecules of the surfactant can be minimized, for example, by providing the hose 65 with a hydrophilic internal coating and a hydrophobic external coating.

The sample volume 1 in the chamber 8 is positioned by means of the manual mechanical stage 85 and the motor driven micrometer screw 86. That can be accomplished automatically by software based control.

Figure 5:
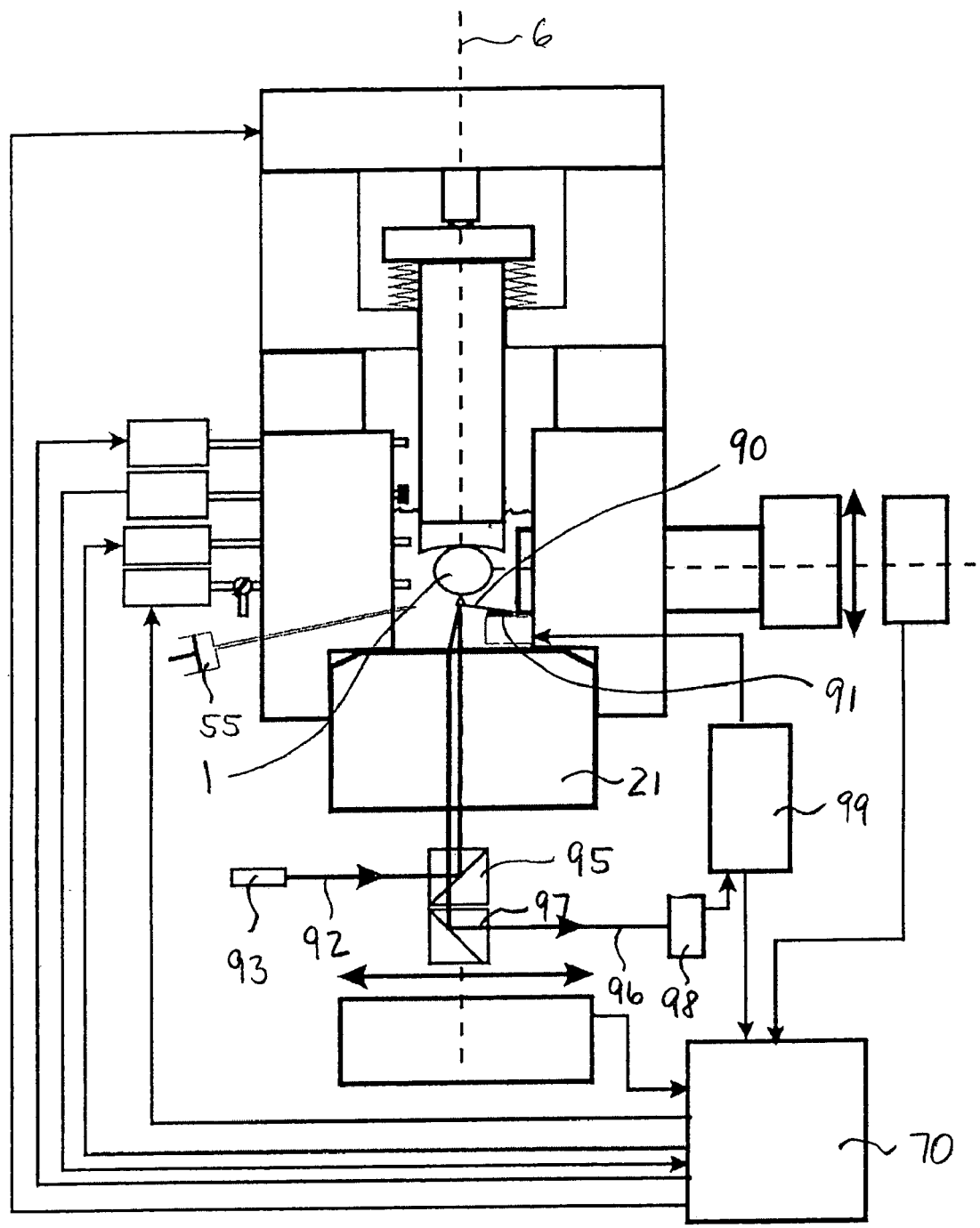
FIG. 5 is a diagrammatic illustration of another captive bubble surfactometer, comprising a raster force microscope to study a surface film.

FIG. 5 is a diagrammatic illustration of another captive bubble surfactometer, the microscope in this embodiment being a raster force microscope (SFM—"scanning force microscopy"). Another type of raster scanning microscope may be provided in another embodiment, such as an optical near field microscope (SNOM—"scanning near field microscopy"). In the preferred embodiment, the cantilever 90 is mounted on a piezo 91 which in turn is attached to the chamber 8. Alternatively, the piezo also could be secured to the objective 21. The piezo must be of such nature as to be able to move the cantilever 90 in all three directions in space so that raster movement may be effected across the surface and, at the same time, the distance be maintained such as required for the respective type of imaging. X nd Y designate displacements at right angles to the optical axis 6, while Z hereinafter designates the axis parallel to the same. An embodiment of a small piezo tube known with raster scanning microscopy would be suitable, for instance. Alternatively, the piezo might scan in lateral direction only (X and Y), and the displacement in vertical direction (Z-axis) could be imparted by a piezo fixed to the plunger. In that event, the air bubble itself would be displaced in vertical direction. Of course, the air bubble also might be moved in all three directions in space. In the embodiment shown, the cantilever deflection can be detected successfully by the light pointer principle which is widely used in raster force microscopy. A beam splitter 95 directs the laser beam 92 of a laser 93 at the cantilever. Here, the objective 21 serves to focus the laser beam on the cantilever. The reflected beam 96 is directed through another beam splitter 97 at a 4-segment diode 98. Control electronics 99 evaluate the signals from the photodiode and control the deflection of the piezo accordingly. The signals, moreover, are passed on to the PC for evaluation. In principle, any known measuring mode of raster scanning microscopy may be performed at the interface.

FIG. 6 shows another embodiment, illustrating a very simple application of the method to a drop of liquid 1 which is surrounded, for example, by gas. Immobility of the surface film is assured once more by virtue of the axially symmetric configuration. The substrate 45 might consist, for instance, of "Teflon" if the medium 1 is hydrophilic, or of agar gel if the liquid is hydrophobic. In this manner it would be guaranteed that the interface at the point of contact is disturbed only a little. Again the outline of the drop may be drawn upon, by observation from the side 31, to determine the surface tension. In this embodiment an upright microscope including the objective 21 might be used, and optimum adjustment of the object and the drop in relation to each other be obtained by conventional adjusting means. Variation of the surface could be obtained by way of a syringe 48 which, however, would disturb the interface and thus make it possible for the creeping described above to occur.

The instant invention, for the first time, presents a measuring method by which a surface active film can be observed microscopically directly at the interface while in an immobile state within the limits of resolution of the respective microscope. Moreover, several apparatus were presented which are suitable for carrying out the method and by which, at the same time, the surface tension can be measured. Also, compression or expansion of the film is possible with simultaneous microscopic observation of selected surface ranges without shifting them out of the image area.

The features of the invention disclosed in the specification above, in the claims and drawing may be essential to implementing the invention in its various embodiments, both individually and in any combination.

What is claimed is:

1. A method of studying properties of a surfactant, the method comprising the following steps:

introducing a first fluid and a second fluid in a measurement chamber and providing the first fluid in a form of a sample volume in the second fluid which is immiscible with the first fluid so that an interface forms between the first fluid and the second fluid at least in a partial area of a surface of the sample volume, the sample volume becoming configured axially symmetrically around a given defining axis so that the interface will be axially symmetrical with respect to the given defining axis;

spreading the surfactant across the interface to form a surface film in the area of the interface; and studying the surface film microscopically, wherein said step of studying the surface film includes using a microscope, and aligning an optical axis of the microscope substantially collinearly with the given defining axis; and varying a gas pressure inside a space above the second fluid in the measurement chamber so that a volume of the sample volume is changed.

2. The method as claimed in claim 1, wherein said step of introducing a first fluid in a form of a sample volume includes providing the sample volume with an essentially spherical shape so that the interface will form on a spherical surface.

3. The method as claimed in claim 1, wherein said step of introducing a first fluid in a form of a sample volume includes forming an interface between the first fluid and the second fluid as a closed layer.

4. The method as claimed in claim 1, wherein said step of introducing a first fluid in a form of a sample volume includes introducing the sample volume by a capillary tube.

5. The method as claimed in claim 1, wherein said step of introducing a first fluid in a form of a sample volume includes applying the sample volume to a support surface, which is curved, for positioning of the sample volume in the second fluid.

6. The method as claimed in claim 1, further comprises the step of varying the sample volume in the course of the microscopic study of the surface film so as to at least one of enlarge and reduce the interface.

7. The method as claimed in claim 1, wherein said step of studying the surface film microscopically includes using a raster scan microscope.

8. The method as claimed in claim 1, wherein said step of varying a gas pressure includes using a dispenser pump to vary the gas pressure inside the space above the second fluid.

9. The method as claimed in claim 1, wherein said step of studying the surface film microscopically includes measuring a surface tension of the surface film.

10. The method as claimed in claim 9, wherein said step of measuring a surface tension includes measuring a pressure-surface isotherm of the surface tension.

11. The method as claimed in claim 9, wherein said step of studying the surface film microscopically includes using a captive bubble surfactometer.

12. The method as claimed in claim 9, wherein said step of studying the surface film microscopically includes using a pulsating bubble surfactometer.

13. An apparatus for studying properties the apparatus comprising the following features:
a measurement chamber which is filled at least partly with a first fluid and a second fluid;
an introducing means for introducing a sample volume of a first fluid in the second fluid which is immiscible with the first fluid so that an interface forms between the first fluid and the second fluid at least in a partial area of a surface of the sample volume, the sample volume becoming configured axially symmetrically around a given defining axis so that the interface will be axially symmetrical with respect to the given defining axis;
a microscope means for microscopic study of a surface film in an area of the interface, wherein said microscope means includes an optical axis that is aligned substantially collinearly with the given defining axis; and
a positioning means for indirectly shifting the first fluid in directions along an X-axis and a Y axis by moving the sample volume.

14. The apparatus as claimed in claim 13, further comprises a spreading means for introducing a surfactant in said measurement chamber so as to form a surface film in the area of the interface.

15. The apparatus as claimed in claim 13, wherein a volume of the measurement chamber can be varied.

16. The apparatus as claimed in claim 13, wherein the sample volume can be shifted by said positioning means along an X-axis, a Y-axis, and a Z-axis of said measurement chamber.

17. The apparatus as claimed in claim 13, further comprises feeding means for introducing the second fluid in the measurement chamber, said feeding means being passed in pressure and vacuum tight fashion through a wall of said measurement chamber.

18. The apparatus as claimed in claim 13, wherein said introducing means for introducing the sample volume comprise a capillary tube by which the sample volume is set upon introduction in said measurement chamber.

19. The apparatus as claimed in claim 13, wherein said microscope means comprises a light microscope.

20. The apparatus as claimed in claim 13, further comprises a device for measuring a surface tension of the surface film.

21. The apparatus as claimed in claim 13, wherein said microscope means comprises a raster scan microscope.

22. The apparatus as claimed in claim 13, further comprises a positioning means for positioning the sample volume in the measurement chamber with respect to said microscope means.

23. The apparatus as claimed in claim 22, wherein said positioning means comprises a positioning element which has a curved support surface for self-positioning of the sample volume.

* * * * *